United States Patent
Mallard et al.

(10) Patent No.: US 10,702,466 B2
(45) Date of Patent: Jul. 7, 2020

(54) EMULSIONS COMPRISING AT LEAST ONE RETINOID AND BENZOYL PEROXIDE

(75) Inventors: Claire Mallard, Mougins (FR); Fabienne Louis, Villeneuve-Loubet (FR); Nathalie Willcox, Saint Vallier de Thiey (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 1214 days.

(21) Appl. No.: 12/457,774

(22) Filed: Jun. 22, 2009

(65) Prior Publication Data

US 2009/0318550 A1   Dec. 24, 2009

Related U.S. Application Data

(63) Continuation of application No. PCT/FR2007/052606, filed on Dec. 21, 2007.

(30) Foreign Application Priority Data

Dec. 21, 2006  (FR) ...................... 06 55783

(51) Int. Cl.
| | |
|---|---|
| A61K 31/185 | (2006.01) |
| A61K 8/67 | (2006.01) |
| A61Q 19/08 | (2006.01) |
| A61K 31/192 | (2006.01) |
| A61Q 19/00 | (2006.01) |
| A61K 8/38 | (2006.01) |
| A61K 31/327 | (2006.01) |
| A61K 8/37 | (2006.01) |

(52) U.S. Cl.
CPC .............. *A61K 8/671* (2013.01); *A61K 8/37* (2013.01); *A61K 8/38* (2013.01); *A61K 31/185* (2013.01); *A61K 31/192* (2013.01); *A61K 31/327* (2013.01); *A61Q 19/00* (2013.01); *A61Q 19/08* (2013.01)

(58) Field of Classification Search
USPC .......................................... 424/443; 514/533
See application file for complete search history.

(56) References Cited

U.S. PATENT DOCUMENTS

| | | | |
|---|---|---|---|
| 3,535,422 A | 10/1970 | Cox et al. | |
| 3,906,108 A | 9/1975 | Felty | |
| 4,189,501 A | 2/1980 | Fulton, Jr. | |
| 4,355,028 A | 10/1982 | Kligman et al. | |
| 4,717,720 A | 1/1988 | Shroot et al. | |
| 4,725,429 A * | 2/1988 | Scott ............... | A61K 8/0229 424/47 |
| 5,035,890 A | 7/1991 | Braun | |
| 5,204,093 A | 4/1993 | Victor | |
| 5,306,486 A | 4/1994 | McCook et al. | |
| 5,665,364 A | 9/1997 | McAtee et al. | |
| 5,707,635 A | 1/1998 | Deckner et al. | |
| 5,733,886 A | 3/1998 | Baroody et al. | |
| 6,010,706 A | 1/2000 | Candau et al. | |
| 6,274,151 B1 | 8/2001 | Michel et al. | |
| 6,413,536 B1 | 7/2002 | Gibson et al. | |
| 6,423,324 B1 | 7/2002 | Murphy et al. | |
| 6,559,189 B2 | 5/2003 | Baker et al. | |
| 7,060,732 B2 * | 6/2006 | Vishnupad et al. ........... 514/725 | |
| 7,368,122 B1 * | 5/2008 | Dow ..................... | A61K 8/06 424/407 |
| 7,700,076 B2 | 4/2010 | Tamarkin et al. | |
| 7,820,186 B2 | 10/2010 | Orsoni et al. | |
| 7,964,202 B2 | 6/2011 | Orsoni et al. | |
| 8,105,618 B2 | 1/2012 | Orsoni-Segona et al. | |
| 8,241,649 B2 | 8/2012 | Orsoni et al. | |
| 8,445,543 B2 | 5/2013 | Abou-Chacra Vernet et al. | |
| 8,568,704 B2 | 10/2013 | Mallard et al. | |
| 8,785,420 B2 | 7/2014 | Abou Chacra Vernet et al. | |
| 8,937,098 B2 | 1/2015 | Mallard et al. | |
| 2002/0035161 A1 | 3/2002 | Segura et al. | |
| 2002/0039561 A1 * | 4/2002 | Doughty .................. | A61K 8/60 424/59 |
| 2002/0064541 A1 | 5/2002 | Lapidot et al. | |
| 2002/0165286 A1 * | 11/2002 | Hedeman ............. | A61K 9/0014 514/785 |
| 2003/0021855 A1 * | 1/2003 | Perricone ............. | A61K 8/0208 424/705 |
| 2003/0157138 A1 | 8/2003 | Eini et al. | |
| 2003/0170196 A1 | 9/2003 | Orsoni et al. | |

(Continued)

FOREIGN PATENT DOCUMENTS

| | | |
|---|---|---|
| EP | 0 199 636 A1 | 10/1986 |
| FR | 2225167 A1 | 11/1974 |

(Continued)

OTHER PUBLICATIONS

International Search Report dated Sep. 16, 2008, by the European Patent Office as the International Searching Authority for International Application No. PCT/FR 2007/052606 filed Dec. 21, 2007, 7 pages.

Sun et al., Development and Application of dermatological drugs for external application, China Science and Technology Press, Jun. 2005, pp. 77-82 and partial English translation (5 pages).

"Community-based trial results of combination acne therapy in subjects with skin of color: Postinflammatory hyperpigmentation", Taylor, Journal of the American Academy of Dermatology, C.V. Mosby, St. Louis, MO, vol. 58, No. 2, Feb. 1, 2008, p. AB13, XP022456844, ISSN: 0190-9622.

"Utilizing Combination Therapy for Ethnic Skin", Cutis, Excerpta Medica, Belle Mead, NJ, US, vol. 80, No. 1, Jul. 1, 2007, pp. 15-20, XP009120299, ISSN: 0011-4162.

(Continued)

*Primary Examiner* — Marcos L Sznaidman
(74) *Attorney, Agent, or Firm* — Foley & Lardner LLP; Sunit Talapatra

(57) ABSTRACT

Stable dermatological/cosmetic emulsions useful, e.g., for the treatment of acne vulgaris, contain, formulated into a physiologically acceptable medium, a homogeneous dispersion of at least one dispersed retinoid, dispersed benzoyl peroxide, at least one fatty phase, at least one hydrophilic phase and at least one emulsifier.

34 Claims, No Drawings

(56) References Cited

U.S. PATENT DOCUMENTS

| | | | |
|---|---|---|---|
| 2004/0167223 A1* | 8/2004 | Popp | A61K 9/0014 514/568 |
| 2005/0074414 A1 | 4/2005 | Tamarkin et al. | |
| 2005/0148495 A1* | 7/2005 | Lambert, Jr. | A61K 8/64 514/18.6 |
| 2005/0163731 A1 | 7/2005 | Pelisson et al. | |
| 2005/0238612 A1 | 10/2005 | Courcoux et al. | |
| 2005/0239043 A1* | 10/2005 | Harding | A61K 8/66 435/4 |
| 2005/0239723 A1 | 10/2005 | Amin et al. | |
| 2006/0128808 A1* | 6/2006 | Arsonnaud | A61K 31/167 514/569 |
| 2006/0234981 A1* | 10/2006 | Baker et al. | 514/64 |
| 2007/0003585 A1 | 1/2007 | Clark et al. | |
| 2007/0044810 A1 | 3/2007 | Ramirez et al. | |
| 2007/0237724 A1 | 10/2007 | Abram et al. | |
| 2009/0191245 A1 | 7/2009 | Fredon et al. | |
| 2009/0226380 A1 | 9/2009 | Clark et al. | |
| 2009/0298798 A1 | 12/2009 | Abou-Chacra Vernet et al. | |
| 2010/0143445 A1 | 6/2010 | Pelisson et al. | |
| 2012/0115947 A1 | 5/2012 | Chacra Vernet et al. | |

FOREIGN PATENT DOCUMENTS

| | | |
|---|---|---|
| FR | 2687312 | 8/1993 |
| FR | 2718018 A1 | 10/1995 |
| FR | 2730930 A1 | 8/1996 |
| FR | 2833841 A1 | 6/2003 |
| FR | 2909000 A1 | 5/2008 |
| FR | 2910321 A1 | 6/2008 |
| GB | 2 088 717 A | 6/1982 |
| GB | 2 130 486 A | 6/1984 |
| WO | WO-81/00206 A | 2/1981 |
| WO | WO-93/07856 | 4/1993 |
| WO | WO 93/20796 | 10/1993 |
| WO | WO-93/20796 A | 10/1993 |
| WO | WO 99/44586 * | 3/1998 |
| WO | 99/44586 A1 | 9/1999 |
| WO | WO 1999/44596 * | 9/1999 |
| WO | WO 03/055472 * | 7/2003 |
| WO | WO 2003/055472 | 7/2003 |
| WO | WO-03/075908 A1 | 9/2003 |
| WO | WO-2004/064833 A1 | 8/2004 |
| WO | 2006/099192 A2 | 9/2006 |
| WO | WO-2007/002831 A | 1/2007 |
| WO | WO-2007/007198 | 1/2007 |
| WO | WO-2007/092312 A2 | 8/2007 |
| WO | WO-2008/006888 A1 | 1/2008 |
| WO | WO-2008/007224 A2 | 1/2008 |
| WO | WO-2008/008397 | 1/2008 |
| WO | WO-2008/087354 | 7/2008 |
| WO | WO-2009/068610 | 6/2009 |
| WO | WO-2009/069006 A2 | 6/2009 |
| WO | WO-2009/130326 A1 | 10/2009 |
| WO | WO-2011/038446 A1 | 4/2011 |
| WO | WO-2011/098391 | 8/2011 |
| WO | WO-2011/135090 | 11/2011 |
| WO | WO 2003/055472 * | 7/2013 |
| WO | WO-2015/091828 | 6/2015 |

OTHER PUBLICATIONS

"Wetting agents" (http://www.innovateus.net/print/science/what-are-wetting-agents) accessed Jan. 23, 2015 (Year: 2015).
Alirezai et al: "Etude Comparative De L'Efficacite et de La Tolerance de Gels D'Adapalene A O, 1 et 0,03, P.100 et D'un Gel de Tretinoine A 0, 025 P.100 Dans le Traitement de L'acne" Annales de Dermatologie et de Venereologie, Paris, FR, vol. 123, No. 3, 1996, pp. 165-170, XP000974556, ISSN: 0151-9638.
Ashland Inc. Ashland Carbomer, Published before 2001, pp. 1-8.
Bikowski, "Clinical Experience Results with Clindamycin 1% Benzoyl Peroxide 5% Gel (Duac®) as Monotherapy and in Combination", Journal of Drugs in Dermatology, Mar. 2005, pp. 164-171, vol. 4, No. 2.
Brand et al., "Cumulative irritancy comparison of adapalene gel 0.1% versus other retinoid products when applied in combination with topical antimicrobial agents", J. Am. Acad. Dermatol., Sep. 2003, pp. S227-S232, vol. 49, No. 3, Cranbury, NJ.
Callender, V D et al., "A meta-analysis to investigate the relation between Fitzpatrick skin types and tolerability of adapalene-benzoyl peroxide topical gel in subjects with mild or moderate acne," Journal of Clinical and Aesthetic Dermatology, 2010, Matrix Medical Communications, USA, vol. 3, No. 8, Jul. 2010, pp. 15-19.
Capizzi et al., "Skin tolerability and efficacy of combination therapy with hydrogen peroxide stabilized cream and adapalene gel in comparison with benzoyl peroxide cream and adapalene gel in common acne. A randomized, investigator-masked, controlled trial", British Journal of Dermatology, 2004, pp. 481-484, vol. 151, No. 2.
Capizzi, et al., "Efficacy and Safety of Combination Therapy of Hydrogen Peroxide Cream and Adapalene Gel in Comparison with Benzoyl Peroxide Cream and Adapalene in Common Acne," Journal of the American Academy of Dermatology, vol. 50, Issue 3, Supplement 1, p. P18 (Mar. 2004).
Caron et al. "Skin Tolerance of Adapalene 0.1% Gel in Combinatoin with other Topical Antiacne Treatments," Journal of the American Academy of Dermatology. vol. 36, No. 6, Part 2. 1997 pp. S113-S115.
Cassano N et al: "Treatment of inflammatory acne with a combination therapy with lymecycline and adapalene followed by maintenance treatment with adapalene" European Journal of Inflammation 2004 Italy, vol. 2, No. 1 , 2004, pp. 45-52, XP009065182.
Cassano N et al: "Treatment of mild to moderate acne vulgaris with adapalene alone or combined with other anti-acne agents. A multicenter open trial" Giornale Italiano Di Dermatologia E Venereologia 2002 Italy, vol. 137, No. 5, 2002, pp. 369-375, XP009065184.
Clucas et al., "Adapalene 0.1 % gel has low skin irritation potential", Journal of the European Academy of Dermatology and Venereology, Sep. 1998, p. S275, vol. 11, Elsevier Science Publisher.
Coley, M K et al., "Managing Common Dermatoses in Skin of Color," Seminars in Cutaneous Medicine and Surgery, W.B. Saunders, Philadelphia, US, vol. 28, No. 2, Jun. 1, 2009, pp. 63-70, XP026301340, ISSN: 1085-5629, DOI: 10.1016/J.SDER.2009.04.006.
Czernielewski et al. Journal of European Academy of Dermatology and Venerology. Dec. 2001, vol. 15, Supplement 3, pp. 5-12.
Czernielewski, et al., Therapeutics for the Clinician, vol. 70, Oct. 2002, p. 243-248.
Differin Gel Data Sheet, available as of Nov. 1998, pp. 1-5.
Do Nascimento L V Et al: "Single-Blind and Comparative Clinical Study of the Efficacy and Safety of Benzoyl Peroxide 4% Gel (BID) and Adapalene 0.1% Gel (QD) in the Treatment of Acne Vulgaris for 11 Weeks," Journal of Dermatological Treatment, Basingstoke, GB, vol. 14, No. 3, Jan. 1, 2003, pp. 166-171, XP008073256, ISSN: 0954-6634.
Draelos, Z. Dermatologic Therapy, vol. 20, 2007, p. 308-313.
Elmore, "Final report on the safety assessment of aluminum silicate, calcium silicate, magnesium aluminum silicate, magnesium silicate, magnesium trisilicate, sodium magnesium silicate, zirconium silicate, attapulgite, bentonite, Fuller's earth, hectorite, kaolin, lithium magnesium silicate, lithium magnesium sodium silicate, montmorillonite, pyrophyllite, and zeolite." 2003, International Journal of Toxicology, 22 (Suppl. 1), pp. 37-102.
Gollnick et al (British Journal of Dermatology, 2009, 161, pp. 1180-1189).
Gollnick et al. (Evaulation of a maintenance treatment acne vulgaris with adapalene gel, 0.1% JEADV (2004) 18 (Suppl. 2), 193-557).
Healy et al. British Medical Journal. 1994, vol. 308, Iss. 6932, pp. 2-9.
Hercules, "Product Data: Natrosol(r) 250 water soluble hydroxyethylcellulose," 2005, Aqualon, accessed online Nov. 1, 2010 [http://www.in-cosmetics.com/ExhibitorLibrary/108/33015e11.pdf].
Hurwitz. "The Combined Effect of Vitamin A Acid and Benzyl Peroxide in the Treatmetn of Acne". vol. 17 No. 3, Mar. 1976. pp. 585-590.
Jamoulle, Jean Claude et al: "Follicular penetration and distribution of topically applied CD 271, a new napthoic acid derivative

(56) References Cited

OTHER PUBLICATIONS intended for topical acne treatment" Journal of Investigative Dermatology (1990), 94(5), 731-2, XP008010277.
Josaine et al: "Skin distribution and pharmaceutical aspects of adapalene gel." Journal of the American Academy of Dermatology, vol. 36, No. 6, part 2, 1997, pp. S119-S125, XP008010230, ISSN: 0190-09622.
Kang Sewon et al: "Assessment of adapalene gel for the treatment of actinic keratoses and lentigines: a randomized trial." Journal of the American Academy of Dermatology. Jul. 2003, vol. 49, No. 1, Jul. 2003, pp. 83-90, XP002376857.
Kimball, A. B. "Skin Differences, Needs, and Disorders across Global Populations," Journal of Investigative Dermatology Symposium Proceedings (2008) 13, 2-5.
Korkut et al., "Benzoyl Peroxide, Adapalene, and their Combination in the Treatment of Acne Vulgaris", The Journal of Dermatology, 2005, pp. 169-173, vol. 32, No. 3, Edirne, Turkey.
Leyden, James J., "A Review of the Use of Combination Therapies for the Treatment of Acne Vulgaris," Journal of the American Academy of Dermatology, vol. 49, No. 3, pp. S200-S210 (Sep. 2003).
Martin et al., Chemical Stability of Adapalene and Tretinoin when Combined with Benzoyl Peroxide in Presence and in Absence of Visible and Ultraviolet Radiation, Brittish Journal of Dermatology, 1998, pp. 8-11, vol. 139, No. Suppl. 52.
Menlo Dermatology Medical Group and Laser Center, Inc. http://www.mdmg.com/general-dermatology/general-1/.
Menlo, http://www.mdmg.com/general-dermatology/general-1/#hyperpigmentation, 2017.
Michalun et al., "Milady's Skin Care and Cosmetic Ingredients Dictionary," Milady Publishing Company, Albany, NY, p. 175.
Millikan, "Adapalene: an update on newer comparative studies between the various retinoids," International Journal of Dermatology, vol. 39, Issue 10, Oct. 2000, pp. 784-788.
Mills Jr. et al. Comparing 2.5%, 5% and 10% benzoyl peroxide on inflammatory acne vulgaris. In. J. Dermatology. Dec. 1986;25(10);664-667.
Piskin, S. et al. "A review of the use of adapalene for the treatment fo acne vulgaris," Therapeutics and Clinical risk Management, 2007, 3(4), pp. 621-624 (Year: 2007).
Pongjanyakul et al., "Influence of magnesium aluminium silicate on rheological, release and permeation characteristics of diclofenac sodium aqueous gels in-vitro," Journal of Pharmacy and Pharmacology, vol. 57, Issue 4, Apr. 2005, pp. 429-434, abstract.
Rolland et al: "Site-specific drug delivery to pilosebaceous structures using polymeric microspheres." Pharmaceutical Research. United States Dec. 1993, vol. 10, No. 12, Dec. 1993 (Dec. 1993), pp. 1738-1744, XP008010243, ISSN: 0724-8741.
Sepicontrol A5, Aug. 2001, pp. 1-53.
Sepigel (http://www.farmalabor.it/schede/2014/119590.PDF) accessed Dec. 7, 2016, pp. 1-2. (Year: 2016).
Shroot et al: "A new concept of drug delivery for acne." Dermatology (Basel),vol. 196, No. 1, 1998, pp. 165-170, XP008010229, ISSN: 1018-8665.
Talukdar et al. Journal of Pharmaceutical Sciences, May 1996, vol. 85, No. 5, pp. 537-540.
Thomas Fitzpatrick (Arch Dermatol. 1988;124(6):869-871).
Weiss et al., "Adapalene for the treatment of acne vulgaris", Journal of the American Academy of Dermatology, Aug. 1998, pp. S50-S54, vol. 39, No. 2.
Wen-Wen et al., "Clinical efficacy and safety of 5% benzoyl peroxide gel combined with 0.1 % adapalene gel in the treatment of acne vulgaris: a multicenter randomized study", Database Biosis, Biosciences Information Service, Jun. 2003, Database accession No. PREV200300514701, pp. 310-312, vol. 36, No. 6.
Zhang J Z et al: "A successful maintenance approach in inflammatory acne with adapalene gel 0.1 % after an initial treatment in combination with clindamycin topical solution 1% or after monotherapy with clindamycin topical solution 1%." The Journal of Dermatological Treatment. Dec. 2004, vol. 15, No. 6, Dec. 2004, pp. 372-378, XP009065185.

\* cited by examiner

EMULSIONS COMPRISING AT LEAST ONE RETINOID AND BENZOYL PEROXIDE

CROSS-REFERENCE TO PRIORITY/PCT EARLIER APPLICATIONS

This application is a continuation of PCT/FR 2007/052606, filed Dec. 21, 2007 and designating the United States (published in the French language on Jul. 24, 2008 as WO 2008/087348 A2; the title and abstract were also published in English), which claims priority under 35 U.S.C. § 119 of FR 06/55783, filed Dec. 21, 2006, each hereby expressly incorporated by reference in its entirety and each assigned to the assignee hereof.

CROSS-REFERENCE TO COMPANION APPLICATION

U.S. patent application Ser. No. 12/457,788, now U.S. Pat. No. 8,957,112, filed concurrently herewith, is hereby also expressly incorporated by reference and also assigned to the assignee hereof.

BACKGROUND OF THE INVENTION

Technical Field of the Invention

The present invention relates to dermatological compositions in the form of an emulsion comprising, formulated into a physiologically acceptable medium, at least one dispersed retinoid and dispersed benzoyl peroxide.

Description of Background and/or Related and/or Prior Art

The use of several categories of active principles is a therapeutic tool to which recourse is frequently had, in particular, in the treatment of dermatological disorders.

Specifically, different anti-fungals, such as allylamine derivatives, triazoles, antibacterials or anti-microbials, such as, for example, antibiotics, quinolones and imidazoles are conventionally combined in the treatment of dermatological diseases/afflictions. It is also known to admixture peroxides, vitamins D and retinoids in the topical treatment of various pathologies related to the skin or mucous membranes, in particular acne.

The combination of several local treatments (antibiotics, retinoids, peroxides, zinc) is also employed in dermatology to make it possible to enhance the effectiveness of the active principles and to reduce their toxicity (Cunliffe W. J., *J. Dermatol. Treat.*, 2000, 11 (suppl. 2), S13-S14).

The multiple application of different dermatological products may be fairly burdensome and demanding for the patient.

The interest in attempting to obtain a novel treatment which is effective with regard to dermatological conditions in a stable composition which offers a good cosmetic quality, which makes possible a single application and which makes possible a use which is agreeable to the patient is thus understood.

Nothing exists among this range of therapies that would encourage one skilled in this art to combine, in the same composition, benzoyl peroxide and a retinoid.

However, the formulation of such a composition presents several problems.

First of all, the effectiveness of the benzoyl peroxide is related to its decomposition when it is brought into contact with the skin. This is because it is the oxidizing properties of the free radicals produced during this decomposition which result in the desired effect. Consequently, in order for the benzoyl peroxide to maintain an optimum effectiveness, it is important to prevent it from decomposing before use, that is to say during storage.

In point of fact, benzoyl peroxide is an unstable chemical compound, which makes it difficult to formulate it in finished products.

The solubility and the stability of benzoyl peroxide have been studied by Cheliquist et al. in ethanol, propylene glycol and various mixtures of polyethylene glycol 400 (PEG 400) and water (Chellquist E. M. and Gorman W. G., *Pharm Res.*, 1992, Vol. 9, 1341-1346).

Benzoyl peroxide is particularly soluble in PEG 400 and ethanol, as is shown in the following table:

| Solvent | Solubility of benzoyl peroxide (mg/g) |
| --- | --- |
| PEG 400 | 39.6 |
| Ethanol | 17.9 |
| Propylene glycol | 2.95 |
| Propylene glycol/water (75:25) | 0.36 |
| Glycerol | 0.15 |
| Water | 0.000155 |

This document furthermore specifies that the stability of benzoyl peroxide is strongly influenced by the chemical composition of the formulation and by the storage temperature. Benzoyl peroxide is highly reactive and decomposes in solution at low temperature due to the instability of its peroxide bond.

The authors thus find that benzoyl peroxide in solution decomposes more or less rapidly in all the solvents studied according to the type of solvent and its concentration.

The decomposition times of benzoyl peroxide in PEG 400 (0.5 mg/g), in ethanol and in propylene glycol are 1.4, 29 and 53 days respectively at 40° C.

Such a decomposition does not make possible the formulation of a product useful for sale.

Furthermore, it is known that benzoyl peroxide is more stable in water and propylene glycol when it is in suspension (i.e., in the dispersed form), since it is not decomposed after storing for 90 days in these solvents.

Thus, to limit the problem of rapid instability of benzoyl peroxide in solution, it has proven to be advantageous to formulate benzoyl peroxide in the dispersed form.

However, this type of formulation is not completely satisfactory insofar as the benzoyl peroxide is still found to be decomposed in the finished product.

Another difficulty to be overcome in the preparation of a composition comprising both benzoyl peroxide and a retinoid is that the majority of retinoids are particularly sensitive to natural oxidation, to visible light and ultraviolet radiation and, as benzoyl peroxide is a strong oxidizing agent, the chemical compatibility of these compounds in one and the same formulation presents numerous problems of stability from the physical and chemical viewpoint.

A stability study was carried out on two retinoids by combining two commercial products, one comprising a retinoid (tretinoin or adapalene) and the second based on benzoyl peroxide (B. Martin et al., *Br. J. Dermatol.*, (1998) 139, (suppl. 52), 8-11).

The presence of the formulation based on benzoyl peroxide causes very rapid decomposition of the oxidation-sensitive retinoids: 50% of the tretinoin is measured as decomposing in 2 hours and 95% in 4 hours. In the composition in which the retinoid is adapalene, no decomposition of the adapalene was measured during 24 hours. This study confirms that benzoyl peroxide is decomposed and decomposes oxidation-sensitive retinoids over time by gradually releasing benzoic acid in finished products.

In point of fact, it is clear that the decomposition of benzoyl peroxide and retinoids is not desirable insofar as it is harmful to the effectiveness of the composition in which they are present.

Nothing would suggest combining of these two active agents to obtain a stable composition of emulsion type, it being known that it was conventionally recognized that the presence of benzoyl peroxide chemically and physically destabilized this type of composition.

The formulation as a "light" emulsion of benzoyl peroxide and a retinoid is advantageous for topical treatments, such as that of acne, as, while contributing emollience, it avoids in particular leaving an excessively greasy feel remaining on the skin.

The term "light emulsion" means an emulsion comprising a low proportion of fatty phase, the aqueous phase remaining predominant.

The term "emulsion" means a liquid system comprising two fluids which are insoluble or virtually insoluble in one another and in which one of the fluids is dispersed in the other as microscopic particles. Preferably, the emulsions used comprise at least one emulsifier, a polar hydrophilic, preferably aqueous, phase and a non-polar fatty phase. Preferably, they are provided in the form of "oil-in-water" (O/W) or "water-in-oil" (W/O) emulsions.

A cream is a formulation which comprises water and oil and is stabilized with an emulsifier. Lipophilic creams are "water-in-oil" (W/O) emulsions and hydrophilic creams are known as "oil-in-water" (O/W) emulsions. W/O creams generally have absorbent bases (petrolatum, ceresin, lanolin, and the like). O/W creams have as base mono-, di- and triglycerides of fatty acids or fatty alcohols with soap, alkyl sulfates or ethers of alkyl polycyclols used as emulsifiers.

The creams can recreate a disrupted hydrolipidic film or can rehydrate the horny layer by virtue of their occlusive power. They can also act as protective cleaning agents or as vehicles for transporting therapeutic substances.

In point of fact, another difficulty to be overcome in the preparation of such a composition comprising in particular dispersed active principles, such as adapalene and benzoyl peroxide, is the sedimentation of the active principles. For if the final feel of such a formulation is obviously related to the sense of the emulsion and to its composition, a light emulsion will rather be oriented O/W and the fatty substances, such as petrolatum, waxes and mineral oils, will be limited, the viscosity playing an important role. Thus, a light emulsion will preferably be fluid, indeed even sprayable. In the case of a more viscous emulsion, the thickeners of the fatty phase, such as solid fatty alcohols and esters, will be greatly reduced, to the advantage of gelling agents in the aqueous phase. In point of fact, the majority of gelling agents for the aqueous phase are destabilized by the benzoic acid released during the decomposition of the benzoyl peroxide.

Specifically, the thickening agents most commonly used for the formulation of gels with benzoyl peroxide are acrylic acid polymers (Carbomer) and celluloses, alone or in combination with silicates.

In point of fact, the use of carbomers in compositions of aqueous gel type does not give good results in terms of chemical stability of the benzoyl peroxide and in terms of rheological stability. As described by Bollinger (Bollinger, Journal of Pharmaceutical Science, 1977, vol. 5), a loss of 5 to 20% of benzoyl peroxide after 2 months at 40° C., depending on the neutralizing agent of the carbomer used, was observed. Furthermore, the release of benzoic acid brings about depolymerization of the carbomers, giving a fall in viscosity which may bring about phase separation.

This instability of benzoyl peroxide gels is harmful to their effectiveness and to their cosmetic quality and it is highly probable that it is reencountered in gel emulsions.

Furthermore, a finished product, in particular when it concerns pharmaceutical or cosmetic compositions, must maintain, throughout its lifetime, precise physicochemical criteria which make it possible to guarantee its pharmaceutical or cosmetic quality respectively. Among these criteria, it is necessary for the rheological properties to be retained. They define the behavior and the texture of the composition during application but also the properties of release of the active principle [SFSTP Commission report 1998] and the homogeneity of the product when the active principles are present therein in the dispersed state.

The need thus exists to have available a physically and chemically stable cream or fluid emulsion of lotion type comprising benzoyl peroxide and a retinoid.

SUMMARY OF THE INVENTION

Dermatological compositions have now been developed which meet this need in the form of emulsions which comprise dispersed benzoyl peroxide, in particular in the free or encapsulated form, at least one retinoid, at least one emulsifier and, when it is gelled, a pH-independent gelling agent and which has good physical stability, that is to say which does not exhibit a drop in viscosity over time and at temperatures of from 4° C. to 40° C., and which maintains good chemical stability for the two active principles (benzoyl peroxide and retinoid), that is to say that decomposition of active principles over time and at temperatures from 4° C. to 40° C. is not observed.

It has now surprisingly been determined that it is possible to obtain a perfect dispersion of active principles by following a specific preparation process. This preparation process makes it possible to obtain an optimum particle size and a homogeneous dispersion of the two active principles in the composition while guaranteeing the physical stability of the product.

The present invention thus features dermatological compositions in the form of emulsions comprising, formulated into a physiologically acceptable medium, at least one retinoid and benzoyl peroxide.

The term "physiologically acceptable medium" means a medium compatible with topical application on the skin, superficial body growths and/or mucous membranes.

The compositions of the present invention can be provided in all the formulation forms normally used for topical application and in particular in the form of emulsions with a liquid consistency (in particular compatible with a presentation of impregnated wipes type) or semiliquid consistency of the milk type, obtained by dispersion of a fatty phase in an aqueous phase (O/W), or of emulsions with a soft, semiliquid or semisolid consistency of the cream type.

One skilled in this art will take care to select the excipients constituting the compositions according to the invention as a function of the formulation form desired and so that the advantageous properties of the subject compositions are respected.

DETAILED DESCRIPTION OF BEST MODE AND SPECIFIC/PREFERRED EMBODIMENTS OF THE INVENTION

The present invention thus features particular emulsions comprising:
- a retinoid and benzoyl peroxide, in particular in the free or encapsulated form;
- at least one hydrophilic phase;
- at least one fatty phase;
- at least one emulsifier.

More particularly, the hydrophilic phase of the compositions according to the invention as defined above is an aqueous phase.

The compositions according to the invention are, more particularly, physically and chemically stable.

The compositions according to the invention can in particular comprise, in addition to at least one retinoid, benzoyl peroxide and at least one emulsifier, one or more of the following ingredients:
- a) one or more gelling agents and/or suspending agents and/or pH-independent gelling agents,
- b) one or more chelating agents,
- c) one or more wetting agents,
- d) one or more lipophilic excipients composing the fatty phase,
- e) an aqueous phase,
- f) one or more additives.

The compositions according to the invention are preferably in the form of an oil-in-water (O/W) emulsion.

To obtain this essential stabilization, an emulsifier is introduced which reduces the surface tension from the two phases. Because they correspond to the physiological requirements of the skin and make it possible for water-soluble substances to uniformly penetrate like oil-soluble substances, emulsions have an important role in dermatological and cosmetic products.

The preferred concentrations of emulsifiers are from 0.001% to 20% by weight, with respect to the total weight of the composition. More preferably, the concentration ranges from 1% to 15% by weight and preferably from 3% to 11% by weight, with respect to the total weight of the composition.

The emulsifiers are amphiphilic compounds which have a hydrophobic part having an affinity for the oil and a hydrophilic part having an affinity for the water, thus creating a connection from the two phases. Ionic or nonionic emulsifiers thus stabilize O/W emulsions by being adsorbed at the interface and by forming lamellar layers of liquid crystals.

The emulsifying power of nonionic emulsifiers is closely related to the polarity of the molecule. This polarity is defined by the HLB (Hydrophilic/Lipophilic Balance).

A high HLB indicates that the hydrophilic fraction is predominant and, conversely, a low HLB indicates that the lipophilic part is predominant. For example, HLB values of greater than approximately 10 correspond to hydrophilic surfactants.

Emulsifiers can be categorized, according to their structure, under the generic terms "ionic" (anionic, cationic, amphoteric) or "nonionic". Nonionic emulsifiers are emulsifiers which do not dissociate into ions in water and are thus insensitive to pH variations.

Nonionic emulsifiers are particularly well suited for the preparation of emulsions of oil-in-water type, according to the present invention. Thus, the emulsifying system which is a component of the emulsion of the invention comprises at least one nonionic emulsifier having a hydrophilic predominant fraction, that is to say exhibiting a high HLB of greater than approximately 10.

Exemplary nonionic emulsifiers exhibiting a high HLB are sorbitan esters, such as POE (20) sorbitan monooleate, marketed under the trademark of Tween 80® (HLB=15), or POE (20) sorbitan monostearate, marketed under the trademark of Tween 60® (HLB=14.9), fatty alcohol ethers, such as POE (21) stearyl ether (HLB=15.5), marketed under the trademark Brij 721® by Uniqema, or ceteareth-20, marketed under the trademark of Eumulgin B2® (HLB of 15.5) by Cognis, polyoxyethylene glycol esters, such as glyceryl stearate and PEG 100 stearate, marketed under the trademark of Arlacel 165 FL® (HLB=11) by Uniqema, or PEG 6 stearate and PEG 32 stearate, marketed under the trademark of Tefose 1500® (HLB=10) by Gateffossé, or sugar esters with a high HLB, such as PEG 20 methyl glucose sesquistearate, marketed under the trademark of glucamate SSE20® (HLB=15) by Amerchol, and sucrose laurate, marketed under the trademark of Surfhope C-1216® (HLB=16), and sucrose stearate, marketed under the trademark of Surfhope C-1811® (HLB=11), by Gattefossé.

Preferably, the said nonionic emulsifiers with a high HLB exhibit an HLB of from 10 and 18.

Exemplary nonionic emulsifiers with a low HLB (lipophilic emulsifiers) are sorbitan esters, such as sorbitan monostearate (HLB=4.7), marketed under the trademark of Span 60 by Uniqema, glycerol esters, such as glycerol monostearate, marketed under the trademark of Cutina GMSVPH(HLB=3.8) by Cognis, polyethylene glycol esters, such as PEG-6 isostearate, marketed under the trademark of Olepal Isostearique® (HLB=8) by Gattefossé, or sugar esters with a low HLB, such as methyl glucose sesquistearate, marketed under the trademark of Glucate SS® (HLB=6) by Amerchol, and sucrose dilaurate, marketed under the trademark of Surfhope C-1205® (HLB=5), and sucrose tristearate, marketed under the trademark of Surfhope C-1803® (HLB=3), by Gattefossé.

Preferably, the said nonionic emulsifiers exhibiting a low HLB exhibit an HLB of less than 10.

The nonionic emulsifiers can be used alone or as a mixture of two or more of them to form the emulsifying system which is a component of the emulsion of the invention.

Use will preferably be made, as emulsifying system, of one or more "nonionic emulsifier with a high HLB"/"nonionic emulsifier with a low HLB" pairs; the system can in particular be a nonionic emulsifying system comprising at least one nonionic emulsifier exhibiting an HLB of greater than approximately 10 and at least one nonionic emulsifier exhibiting an HLB of less than approximately 10.

The ratio of each of the two emulsifiers forming the abovementioned pair is generally determined by the calculation of the HLB required for the fatty phase used.

Exemplary preferred emulsifiers are hydrophilic emulsifiers of the following types: glyceryl stearate & PEG-100 stearate, marketed under the trademark Arlacel 165FL® by Uniqema, PEG 6 stearate and PEG 32 stearate, marketed under the trademark of Tefose 1500® by Gattefossé, PEG 20 methyl glucose sesquistearate, marketed under the trademark of Glucamate SSE 20® by Amerchol, polyoxyethylene (21) stearyl ether, marketed under the trademark Brij 721® by Uniqema, and ceteareth-20, marketed under the trademark of Eumulgin B2PH® by Cognis; or of lipophilic emulsifiers of methyl glucose sesquistearate type, such as Glucate SS®, marketed by Amerchol.

The compositions according to the invention comprise at least one retinoid. The term "retinoid" means any compound which binds to RAR and/or RXR receptors.

Exemplary retinoids are retinoic acid, tretinoin, tazarotene and those described in the following:

U.S. Pat. Nos. 4,666,941, 4,581,380, EP 0,210,929, EP 0,232,199,
EP 0,260,162, EP 0,292,348, EP 0,325,540, EP 0,359,621, EP 0,409,728, EP 0,409,740, EP 0,552,282, EP 0,584,191, EP 0,514,264, EP 0,514,269, EP 0,661,260, EP 0,661,258, EP 0,658,553, EP 0,679,628, EP 0,679,631, EP 0,679,630, EP 0,708,100, EP 0,709,382, EP 0,722,928, EP 0,728,739, EP 0,732,328, EP 0,749,937, EP 0,776,885, EP 0,776,881, EP 0,823,903, EP 0,832,057, EP 0,832,081, EP 0,816,352, EP 0,826,657, EP 0,874,626, EP 0,934,295, EP 0,915,823, EP 0,882,033, EP 0,850,909, EP 0,879,814, EP 0,952,974, EP 0,905,118, EP 0,947,496, WO98/56783, WO99/10322, WO99/50239, WO99/65872.

Due to their ability to bind RAR and/or RXR receptors, the compounds resulting from the family of the benzonaphthalene retinoids, such as described in EP 0,199,636, are also included in the invention.

Preferably, the naphthoic acid derivatives will be selected and in particular:

6-(3-methylphenyl)-2-naphthoic acid and its methyl ester,
6-(4-(tert-butyl)phenyl)-2-naphthoic acid and its methyl ester,
6-(3-(tert-butyl)phenyl)-2-naphthoic acid and its methyl ester,
6-(3,4-dimethoxyphenyl)-2-naphthoic acid and its methyl ester,
6-(p-(1-adamantylthio)phenyl)-2-naphthoic acid and its methyl ester,
6-(3-(1-adamantyl)-4-methoxyphenyl)-2-naphthoic acid (adapalene) and its methyl ester,
the methyl ester of 6-[3-(1-adamantyl)-4-(tert-butyldimethylsilyloxy)phenyl]-2-naphthoic acid,
the methyl ester of 6-[3-(1-adamantyl)-4-hydroxyphenyl]-2-naphthoic acid,
6-[3-(1-adamantyl)-4-hydroxyphenyl]-2-naphthoic acid,
the methyl ester of 6-[3-(1-adamantyl)-4-decyloxyphenyl]-2-naphthoic acid,
6-[3-(1-adamantyl)-4-decyloxyphenyl]-2-naphthoic acid,
the methyl ester of 6-[3-(1-adamantyl)-4-hexyloxyphenyl]-2-naphthoic acid,
6-[3-(1-adamantyl)-4-hexyloxyphenyl]-2-naphthoic acid,
the methyl ester of 6-[3-(1-adamantyl)-4-methoxyphenyl]-4-acetoxy-1-methyl-2-naphthoic acid,
6-[3-(1-adamantyl)-4-methoxyphenyl]-4-hydroxy-1-methyl-2-naphthoic acid,
the methyl ester of 6-[3-(1-adamantyl)-4-methoxyphenyl]-4-hydroxy-1-methyl-2-naphthoic acid,
the methyl ester of 6-[3-(1-adamantyl)-4-methoxyphenyl]-1-methyl-2-naphthoic acid,
6-[3-(1-adamantyl)-4-methoxyphenyl]-1-methyl-2-naphthoic acid,
6-[3-(1-adamantyl)-4-methoxyphenyl]-2-naphthalenemethanol,
the ethyl amide of 6-[3-(1-adamantyl)-4-methoxyphenyl]-2-naphthoic acid,
the morpholide of 6-[3-(1-adamantyl)-4-methoxyphenyl]-2-naphthoic acid,
the methyl ester of 6-[3-(tert-butyl)-4-methoxyphenyl]-2-naphthoic acid,
6-[3-(tert-butyl)-4-methoxyphenyl]-2-naphthoic acid,
the methyl ester of 6-[3-(1,1-dimethyldecyl)-4-methoxyphenyl]-2-naphthoic acid,
6-[3-(1,1-dimethyldecyl)-4-methoxyphenyl]-2-naphthoic acid.

In particular, preference will be given to adapalene and its salts.

The term "salts of adapalene" means the salts formed with a pharmaceutically acceptable base, in particular inorganic bases, such as sodium hydroxide, potassium hydroxide and ammonia, or organic bases, such as lysine, arginine or N-methylglucamine.

The term "salts of adapalene" is also understood to mean the salts formed with fatty amines, such as dioctylamine and stearylamine.

Of course, the amount of the two active agents, benzoyl peroxide and retinoid, in the composition according to the invention will depend on the combination selected and thus particularly on the retinoid under consideration and on the quality of the treatment desired.

The preferred retinoid concentrations are from 0.0001% to 20% by weight, with respect to the total weight of the composition.

Preferably, in the case of adapalene, the compositions according to the invention comprise from 0.001% to 5% by weight and advantageously from 0.01% to 1% by weight of adapalene, with respect to the total weight of the composition, preferentially from 0.01% to 0.5% by weight, preferably from 0.1% to 0.4% by weight of adapalene, more preferably still 0.3% by weight of adapalene.

The benzoyl peroxide can just as easily be employed in the free form or else in an encapsulated form, for example in a form adsorbed on or absorbed in any porous support. It can, for example, be benzoyl peroxide encapsulated in a polymeric system composed of porous microspheres, such as, for example, microsponges marketed under the trademark of Microsponges P009A Benzoyl Peroxide® by Cardinal Health.

To provide an order of magnitude, the compositions according to the invention advantageously comprise from 0.0001% to 20% by weight of benzoyl peroxide and from 0.0001% to 20% by weight of retinoid, with respect to the total weight of the composition, and preferably from 0.025% to 10% by weight of benzoyl peroxide and from 0.001% to 10% by weight of retinoid respectively, with respect to the total weight of the composition.

For example, in the compositions for the treatment of acne, the benzoyl peroxide is preferably included at concentrations ranging from 2% to 10% by weight and more particularly from 2.5% to 5% by weight, with respect to the total weight of the composition. The retinoid for its part is included in this type of composition at concentrations generally ranging from 0.01% to 1% by weight, with respect to the total weight of the composition.

Advantageously, the particle size of the retinoid and of the benzoyl peroxide is such that at least 80% by number of the particles and preferably at least 90% by number of the particles have a diameter of less than 25 μm and at least 99% by number of the particles have a diameter of less than 100 μm.

The compositions of the invention can comprise one or more wetting agents. These ingredients can be present in concentrations ranging from 0.001% to 20% by weight, preferably from 0.1% to 10% by weight and more preferably from 2% to 7% by weight, with respect to the total weight of the composition. They should not dissolve the active principles at the percentage used, should not cause exothermic reactions harmful to the benzoyl peroxide, should help in dispersing the active principles well and should have anti-foaming properties.

The wetting power is the tendency of a liquid to spread out over a solid surface. By reducing the surface tension, the wetting agents make possible greater spreading of the liquid and thus help in the dispersing of the solid particles of retinoids and benzoyl peroxide.

Preferably, the wetting agents are ones which can exhibit an HLB (Hydrophilic-Lipophilic Balance) of 7 to 18 or else the wetting agents are nonionic surfactants of the type of polyoxyethylenated and/or polyoxypropylenated copolymers (mention will be made, as non-limiting examples, of the Poloxamers and more particularly Synperonic PE/L44 and/or Synperonic PE/L62, marketed by Uniqema), or glycols, such as the propylene glycol, dipropylene glycol, lauroglycol, propylene glycol dipelargonate or ethoxydiglycol. Preferably, the wetting agents are in the liquid form, so as to be easily incorporated in the composition without it being necessary to heat it.

Preferred wetting agents are wetting agents which can preferably exhibit an HLB of 10 to 14, and include compounds of the family of the Poloxamers and/or glycols and more particularly Synperonic PE/L44 and/or Synperonic PE/L62 and/or compounds such as propylene glycol, dipropylene glycol, propylene glycol dipelargonate, lauroglycol or ethoxydiglycol.

The particularly preferred wetting agent is propylene glycol and Synperonic PE/L44 (polyethylene-polypropylene glycol; polyoxyethylene-polyoxypropylene block copolymer).

According to the invention, the emulsion comprising the benzoyl peroxide and a retinoid advantageously comprises at least water and can also comprise a propenetrating agent and/or a wetting agent.

The compositions according to the invention also comprise a fatty phase. This fatty phase can comprise, for example, vegetable, mineral, animal or synthetic oils, silicone oils and mixtures thereof.

Exemplary mineral oils are liquid paraffins with different viscosities, such as Primol 352®, Marcol 82® or Marcol 152®, marketed by Esso.

Exemplary are vegetable oils are sweet almond oil, palm oil, soybean oil, sesame oil or sunflower oil.

Exemplary animal oils are lanolin, squalene, fish oil or mink oil, with, as derivative, the squalane marketed under the trademark Cosbiol® by Laserson.

Exemplary synthetic oils are an ester, such as cetearyl isononanoate, for example the product marketed under the trademark of Cetiol SN PH® by Cognis France, isopropyl palmitate, for example the product marketed under the trademark of Crodamol IPP® by Croda, diisopropyl adipate, marketed under the trademark of Crodamol DA by Croda, or caprylic/capric triglyceride, such as Miglyol 812®, marketed by Hüls/Univar.

Exemplary volatile or non-volatile silicone oils are dimethicones, such as the products marketed under the trademark of Q7-9120 Silicone Fluid with a viscosity from 20 cSt to 12 500 cSt or the product marketed under the trademark ST-Cyclomethicone-5 NF® by Dow Corning.

Solid fatty substances may also be included, such as natural or synthetic waxes, fatty acids, such as stearic acid, fatty alcohols, such as Speziol C18 Pharma, marketed by Cognis, and texturizing agents of tribehenate type, such as Compritol 888, marketed by Gattefossé, or hydrogenated castor oils, such as Cutina HR, marketed by Cognis. In this case, one skilled in this art will adjust the heating temperature of the preparation according to the presence or absence of these solids.

For the compositions according to the invention, synthetic oils and silicone oils and more particularly Miglyol 812® and ST-Cyclomethicone 5 NF® are preferred.

The hydrophilic phase of the emulsions according to the invention is preferably aqueous and thus can comprise water. This water can in particular be a floral water, such as cornflower water, or a natural thermal or mineral water, for example selected from among water from Vittel, waters from the Vichy basin, water from Uriage, water from La Roche-Posay, water from Avène or water from Aix-les-Bains.

The said aqueous phase can be present at a content of from 10% to 90% by weight, with respect to the total weight of the composition, preferably from 20% to 80% by weight.

Exemplary chelating agents are ethylenediaminetetraacetic acid (EDTA), diethylenetriaminepentaacetic acid (DTPA), ethylenediaminedi(o-hydroxyphenylacetic acid) (EDDHA), (2-hydroxyethyl)ethylenediaminetriacetic acid (HEDTA), ethylenediaminedi(o-hydroxy-p-methylphenylacetic acid) (EDDHMA) and ethylenediaminedi(5-carboxy-2-hydroxyphenylacetic acid) (EDDCHA).

The concentrations of chelating agent can vary from 0% to 1.5% by weight, preferably from 0.05% to 0.5% by weight, with respect to the total weight of the composition.

A preferred chelating agent is ethylenediaminetetraacetic acid (EDTA).

Exemplary gelling agents and/or suspending agents and/or pH-independent gelling agents which can be formulated into the compositions according to the invention are microcrystalline cellulose and carboxymethyl cellulose sodium, marketed under the trademark of Avicel CL-611 by FMC Biopolymer, "electrolyte-insensitive" carbomers, marketed under the trademark of Ultrez 20® or 1382 or of Carbopol ETD2020® by Noveon, and also the acrylates/$C_{10-30}$ alkyl acrylate crosspolymer marketed under the trademark of Pemulen TR-1 or Pemulen TR-2, polysaccharides, with, as non-limiting examples, xanthan gum, such as the Xantural 180®, marketed by Kelco, guar gum, chitosans, cellulose and its derivatives, such as hydroxypropylmethylcellulose, in particular the product marketed under the trademark of Methocel E4 Premium by Dow Chemical, or hydroxyethylcellulose, in particular the product marketed under the trademark of Natrosol HHX 250® by Aqualon, or also the product "microcrystalline cellulose and carboxymethyl cellulose sodium" marketed under the trademark of Avicel CL-611 by FMC Biopolymer, the family of aluminum magnesium silicates, such as Veegum K, marketed by Vanderbilt, the family of carrageenans, in particular divided into four main families: κ, λ, β and ω, such as the Viscarin® products and Gelcarin® products marketed by IMCD, the family of acrylic polymers coupled to hydrophobic chains, such as the PEG-150/decyl/SMDI copolymer marketed under the trademark of Aculyn 44 (polycondensate comprising at least, as components, a polyethylene glycol comprising 150 or 180 mol of ethylene oxide, decyl alcohol and methylenebis(4-cyclohexyl isocyanate) (SMDI), at 35% by weight in a mixture of propylene glycol (39%) and water (26%)), the family of modified starches, such as the modified potato starch marketed under the trademark of Structure Solanace, and also their mixtures, and gelling agents of the family of polyacrylamides, such as the sodium acryloyldimethyltaurate copolymer/isohexadecane/polysorbate 80 mixture marketed under the trademark Simulgel 600 PHA by Seppic or the polyacrylamide/C13-14 isoparaffin/laureth-7 mixture, such as, for example, that marketed under the trademark of Sepigel 305 by Seppic.

The preferred gelling agents result from the family of polyacrylamides, such as Simulgel 600 or Sepigel 305; "electrolyte-insensitive" carbomers, such as Carbopol ETD2020 NF; polysaccharides, such as xanthan gum; cellulose derivatives, such as hydroxypropylmethylcellulose or hydroxyethylcellulose; or aluminum magnesium silicates, alone or as a mixture.

The gelling agents and/or suspending agents and/or pH-independent gelling agents as described above can be used at the preferred concentrations ranging from 0.001% to 15% to more preferably ranging from 0.1% to 5%.

The compositions can additionally comprise any additive conventionally used in the cosmetics or pharmaceutical field, such as antioxidants, sunscreens, preservatives, fillers, electrolytes, humectants and/or emollients, colorants, neutralizing agents of normal inorganic or organic base or acid type (by way of example, triethanolamine, 10% sodium hydroxide solution, the succinic acid/sodium succinate buffer or the citric acid/sodium citrate buffer), fragrances, essential oils, cosmetic active principles, moisturizing agents, vitamins, essential fatty acids, sphingolipids, self-tanning compounds, such as DHA, soothing agents and protective agents for the skin, such as allantoin, propenetrating agents, or a mixture of these, optionally a stabilizing agent for benzoyl peroxide (by way of example, sodium docusate or sodium $C_{14-16}$ olefinsulfonate). Of course, one skilled in this art will take care to select this or these optional additional compounds and/or their amounts in such a way that the advantageous properties of the composition according to the invention are not, or not substantially, detrimentally affected.

These additives can be present in the composition in a proportion of 0.001% to 20% by weight, with respect to the total weight of the composition.

Exemplary preservatives are benzalkonium chloride, bronopol, chlorhexidine, chlorocresol and its derivatives, ethyl alcohol, phenethyl alcohol, phenoxyethanol, potassium sorbate, diazolidinylurea, benzyl alcohol, parabens or their mixtures.

Exemplary humectants and/or emollients are glycerol and sorbitol, sugars (by way of example, glucose or lactose), PEGs (by way of example, Lutrol E400), urea or amino acids (by way of example, serine, citrulline or alanine).

In particular, the present invention also features pharmaceutical or cosmetic compositions for topical application to the skin, superficial body growths or mucous membranes in the form of an emulsion comprising, formulated into a physiologically acceptable medium, the ingredients (expressed as percentage by weight) selected from among:

from 0.001% to 5%, preferably from 0.01% to 0.5%, of a retinoid and preferably of a naphthoic acid derivative;
from 0.025% to 10%, preferably from 2% to 10%, of benzoyl peroxide;
from 30% to 95%, preferably from 50% to 85%, of water;
from 0.01% to 15%, preferably from 0.1% to 5%, of gelling agents and/or of suspending agents and/or of pH-independent gelling agents;
from 1% to 15%, preferably from 3% to 11%, of emulsifiers;
from 2% to 50%, preferably from 5% to 30%, of fatty phase;
from 0% to 1.5%, preferably from 0.05% to 0.5%, of one or more chelating agents;
from 0% to 10%, preferably from 2% to 7%, of one or more wetting agents;
from 0.1% to 20%, preferably from 2% to 15%, of one or more humectants and/or emollients;
from 0% to 3%, preferably from 0.05% to 1%, of preservatives;
from 0% to 3%, preferably from 0.05% to 2%, of stabilizing agents;
from 0% to 10%, preferably from 0.1% to 5%, of neutralizing agents.

The present invention also features administration of the compositions as described above as medicament.

The invention also features the use of the novel composition as described above in cosmetics and in dermatology.

Due to the keratolytic, bactericidal and anti-inflammatory activity of benzoyl peroxide and the marked activity of retinoids in the fields of cell differentiation and proliferation, the compositions of the invention are particularly well suited for the following therapeutic fields:

1) for treating dermatological conditions linked to a disorder of keratinization involving differentiation and proliferation, in particular for treating acne vulgaris, comedonic or polymorphic acne, acne rosacea, nodulocystic acne, acne conglobata, senile acne, secondary acnes, such as solar, drug or occupational acne, or hidradenitis suppurativa,
2) for treating other types of disorders of keratinization, in particular ichthyoses, ichthyosiform conditions, Darier's disease, palmoplantar keratoderma, leucoplakia and leucoplakiform conditions, or cutaneous or mucosal (oral) lichen,
3) for treating other dermatological conditions linked to a disorder of keratinization with an inflammatory and/or immunoallergic component and, in particular, all forms of psoriasis, whether cutaneous, mucosal or ungual, and even psoriatic rheumatism, or alternatively cutaneous atopy, such as eczema, or respiratory atopy or alternatively gingival hypertrophy; the compounds can also be used in some inflammatory conditions not exhibiting disorder of keratinization, such as folliculitis,
4) for treating all dermal or epidermal proliferations, whether they are benign or malignant and whether they are or are not of viral origin, such as common warts, flat warts, molluscum contagiosum and epidermodysplasia verruciformis, florid or oral papillomatoses, and the proliferations which can be induced by ultraviolet radiation, in particular in the case of actinic keratoses,
5) for repairing or combating skin ageing, whether photoinduced or chronologic, or for reducing pigmentations, or any pathology associated with chronologic or actinic ageing;
6) for preventively or curatively treating disorders of cicatrization or skin ulcers, for preventing or repairing stretch marks, or alternatively for promoting cicatrization,
7) for combating disorders of the sebaceous function, such as hyperseborrhoea of acne or simple seborrhoea,
8) in the treatment of any condition of fungal origin on the skin, such as tinea pedis and tinea versicolor,
9) in the treatment of dermatological conditions with an immunological component,
10) in the treatment of skin disorders due to exposure to UV radiation, and
11) in the treatment of dermatological conditions linked to inflammation or infection of the tissues surrounding the hair follicle, in particular due to microbial colonization or infection, in particular impetigo, seborrhoeic dermatitis, folliculitis or sycosis barbae, or involving any other bacterial or fungal agent.

The compositions according to the invention are particularly useful for the preventive or curative treatment of acne vulgaris.

This invention also features pharmaceutical compositions useful for the prevention and/or treatment of dermatological conditions linked to disorders of cell differentiation and/or proliferation and/or keratinization, preferably acne vulgaris.

The compositions according to the invention are also useful in the cosmetics field, in particular for the treatment of skin with a tendency towards acne, for hair growth, for combating hair loss, for combating the greasy appearance of the skin or hair, in protecting against the harmful effects of the sun or for preventing and/or for combating photoinduced or chronologic ageing.

The compositions according to the invention are also useful in body and hair hygiene.

Preferably, the said compositions according to the invention are administered topically.

The present invention also features a process for the preparation of a composition as described above. Such a process is characterized in that it comprises a stage of mixing a physiologically acceptable medium with at least one naphthoic acid derivative and benzoyl peroxide.

The other optional excipients and additives will be introduced according to the chemical nature of the compounds and the formulation form selected.

Generally, the formulation of a composition according to the invention takes place, by way of example, according to the following main process:
  a) mixing at least one retinoid with water until it is completely dispersed, to obtain active phase 1;
  b) mixing the benzoyl peroxide with water until it has completely dispersed, to obtain active phase 2;
  c) mixing at least one hydrophilic compound with water, to obtain the aqueous phase;
  d) mixing at least one emulsifier with a lipophilic compound, to obtain the fatty phase;
  e) introducing the fatty phase obtained in d) into the aqueous phase obtained in c), to obtain an emulsion;
  f) introducing active phases 1 and 2, obtained in a) and b) respectively, into the emulsion obtained in e);
  g) if necessary, a neutralizing agent for the gelling agent is introduced into the emulsion obtained in e);
  h) if necessary, the heat-sensitive additives are added;
  i) if necessary, further water is added.

Generally, the preparation of a composition according to the invention takes place, by way of example, according to the following alternative process:
  a') Stages a) and b) are combined, so as to obtain stage a'), which corresponds to the mixing of at least one retinoid, benzoyl peroxide and at least one wetting agent with water until they have completely dispersed, to obtain a single active phase.

Stages c), d), e), f), g), h), i) and j) of the main process remain unchanged.

Preferably, the preparation of a composition according to the invention takes place, by way of example, according to the following main process:
  a) the retinoid, preferably the naphthoic acid derivative, is mixed with at least one wetting agent in water until the active principle has completely dispersed, to obtain active phase 1;
  b) the benzoyl peroxide is mixed with at least one wetting agent in water until it has completely dispersed, to obtain active phase 2;
  c) one or more gelling agents and/or suspending agents and/or pH-independent gelling agents and optionally one or more chelating agents, one or more preservatives and the heat-insensitive hydrophilic additives and one or more humectants and/or emollients are dissolved in the water with stirring, if necessary under hot conditions, stirring is maintained and optionally heating is maintained until homogeneity is achieved, to obtain the aqueous phase;
  d) at least one emulsifier is mixed, under hot conditions, with oils and/or solid fatty substances, optionally with preservatives and the heat-insensitive lipophilic additives, until homogeneity is achieved, to obtain the fatty phase;
  e) the said fatty phase obtained in d) is introduced into the aqueous phase obtained in c), to obtain an emulsion;
  f) the said active phases 1 and 2 obtained in a) and b) respectively are introduced into the emulsion obtained in e), to obtain the active emulsion;
  g) if necessary, a neutralizing agent for the gelling agent is introduced into the emulsion obtained in f), to obtain the desired pH;
  h) if necessary, the heat-sensitive additives are added;
  i) optionally, the copolymer of acrylamide and of sodium acrylamido-2-methylpropanesulfonate, as a 40% dispersion in isohexadecane and polysorbate 80, is added;
  j) if necessary, further water is added.

Preferably, the preparation of a composition according to the invention takes place, by way of example, according to the following alternative process:
  a') Stages a) and b) are combined, so as to obtain stage a'), which corresponds to the mixing of at least one retinoid, benzoyl peroxide and at least one wetting agent with water until they have completely dispersed, to obtain a single active phase.

Stages c), d), e), f, g), h), i) and j) of the main process remain unchanged.

More specifically, the main process for the preparation of the composition according to the invention comprises, by way of example, the following stages:

Stage a: Preparation of Active Phase 1:

Active principle 1, the retinoid (preferably adapalene), a portion of the purified water and the wetting agents (Synperonic PE/L62, Synperonic PE/L44, propylene glycol type) are mixed in a beaker and stirring is allowed to take place until the ingredients have completely dispersed.

Stage b: Preparation of Active Phase 2:

The purified water, the active principle (benzoyl peroxide) and the wetting agents (Synperonic PE/L62, Synperonic PE/L44 and propylene glycol type) are introduced with stirring into a beaker and stirring is allowed to take place until the ingredients have completely dispersed.

Stage c: Preparation of the Aqueous Phase:

Purified water and the gelling agent or agents and/or the pH-independent gelling agent or agents (with the exception of the polyacrylamide) and optionally the chelating agent or agents (EDTA type), the humectant or humectants and/or the emollient or emollients (glycerol type), the preservative or preservatives (methylparaben type), the emulsifiers, the suspending agent or agents (Avicel type) and the stabilizing agent or agents (sodium docusate type) are introduced with stirring, if necessary under hot conditions, into a beaker.

Stage d: Preparation of the Fatty Phase:

The lipophilic emulsifier or emulsifiers (Glucate SS, Glucamate SSE 20, Brij 721, Tefose 1500, Eumulgin B2 PH, Olepal Isostearique type), the oily compounds (Cetiol SN, Crodamol DA, Speziol C18, Miglyol 812, Cosbiol type), the optional heat-insensitive lipophilic additives and optionally the preservatives (phenoxyethanol, propylparaben type) are mixed in a beaker.

Stage e: Emulsification:

The fatty phase is introduced into the aqueous phase under hot conditions with stirring, to bring about emulsification. Heating is maintained for a few minutes and then the product is allowed to gently cool. The stirring is adjusted as a function of the viscosity. It is possible to introduce the volatile silicone, if the latter is present in the composition, from 50° C.

Stage f: Incorporation of Active Phases 1 and 2:

Active phases 1 and 2 are introduced one after the other with stirring at a temperature below 40° C. Stirring is maintained until the mixture is completely homogeneous.

Stage g (Optional): Neutralization:

The neutralization agent for the gelling agent (triethanolamine or 10% sodium hydroxide solution type) or the pH buffer is introduced, if necessary, at a temperature below 40° C. until at the desired pH. The product then assumes a thicker consistency. At the end of the manufacturing operation, the pH is again confirmed. If necessary, the adjustment to 100% with water is carried out. The product is homogenized a final time to ensure the active principles, adapalene and benzoyl peroxide, are satisfactorily dispersed (microscopic observation revealing a homogeneous and aggregate-free dispersion).

Stage h (Optional): Addition of the Other Additives:

The optional additives are introduced with stirring at a temperature below 40° C. Stirring is maintained until the mixture is completely homogeneous.

Stage i (Optional): Addition of the Polyacrylamide:

The polyacrylamide is introduced with stirring at a temperature below 40° C. Stirring is maintained until the mixture is completely homogeneous.

Stage j: Correction of the Water Loss:

The water loss during the preparation of the product is calculated and the lost water is re-added with stirring. Stirring is maintained until the mixture is completely homogeneous.

More specifically, the alternative process for the preparation of the composition according to the invention comprises, by way of example, the following stages:

a') Stages a) and b) are combined, so as to obtain stage a'), which corresponds to the mixing of at least one retinoid, benzoyl peroxide and at least one wetting agent with water until they have completely dispersed, to obtain a single active phase.

Stages c), d), e), f), g), h), i) and j) of the main process remain unchanged.

The present invention will now be illustrated by means of the following examples and of the physical and chemical stability data presented below.

The physical stability of the formulations is measured by macroscopic and microscopic observation of the formulation at ambient temperature and 40° C. at T1 month, T2 month and optionally T+15 days.

At AT, macroscopic observation makes it possible to guarantee the physical integrity of the products.

Microscopic observation makes it possible to evaluate the quality of the dispersion of the two active principles. The adapalene is observed in fluorescent light while the benzoyl peroxide is observed in polarized light.

The characterization of the finished product is completed by a measurement of the yield point and of viscosity.

For the measurement of the point of a Haake rheometer of VT550 type with an SVDIN measuring spindle.

The rheograms are produced at 25° C. and at the shear rate of 4 s$^{-1}$, 20 s$^{-1}$ and 100 s$^{-1}$ ($\gamma$), the shear stress being measured. The term "yield point" ($\tau0$, expressed in pascals) means the force necessary (minimum shear stress) to overcome the cohesive forces of Van der Waals type and to bring about flow. The yield point is to be equated with the value found at the shear rate of 4 s$^{-1}$.

For the viscosity measurements, use is made of viscometers of Brookfield RVDVII+ and LDVDII+ type.

The viscosity ranges which can be measured with the two Brookfield types are as follows:

RVDVII+ viscometer: 100 cP-40 McP
LVDVII+ viscometer: 15 cP-6 McP

It is considered that there is present, at the starting time T0:

a cream if the viscosity is greater than 30 000 cP
a lotion if the viscosity is less than 30 000 cP (Lucinda Bushe, ACPS Oct. 22, 2003, Pharmaceutical nomenclature-Issues and challenges).

The chemical stability is ensured by an HPLC quantitative determination of the active principles.

The result is expressed in g/g of adapalene and of benzoyl peroxide and as % with respect to the expected content.

To further illustrate the present invention and the advantages thereof, the following specific examples are given, it being understood that same are intended only as illustrative and in nowise limitative. In said examples to follow, all parts and percentages are given by weight, unless otherwise indicated.

Example 1

Formulation of Cream Type Comprising 0.1% Adapalene and 2.5% Benzoyl Peroxide

The formulation is prepared according to the procedure described above.

| Constituents | Content (% w/w) |
| --- | --- |
| Benzoyl peroxide | 2.50 |
| Adapalene | 0.10 |
| Propylene glycol | 4.00 |
| Synperonic PE/L44 | 0.20 |
| Sodium docusate | 0.05 |
| Propylene glycol | 2.00 |
| EDTA | 0.10 |
| Carbopol Ultrez 20 | 0.40 |
| Glycerol | 3.00 |
| Glucamate SSE 20 | 3.50 |
| Glucate SS | 3.50 |
| Cosbiol | 6.00 |
| ST-Cyclomethicone 5 NF | 13.00 |
| Purified water | q.s. for 100 |
| Triethanolamine | q.s. for pH 5.5 ± 0.5 |

Stability Data:
Physical Stability:

| Characterizations at T0 | |
| --- | --- |
| Macroscopic appearance | White cream |
| Microscopic appearance | Dispersion of the active principles without aggregates >100 μm |
| pH | 6.07 |
| Viscosity data | Haake (4 s$^{-1}$/20 s$^{-1}$/100 s$^{-1}$) 233/312/418 |
| | Brookfield RVDVII+ (S29; 5 rpm) 184 990 cP |

-continued

Characterizations at T0

|  |  | T + 15 days | T + 1 month | T + 2 months | T + 3 months |
|---|---|---|---|---|---|
| Macroscopic appearance | AT | Identical to T0 | Identical to T0 | Identical to T0 | Identical to T0 |
|  | 40° C. | Identical to T0 | Identical to T0 | Identical to T0 | Identical to T0 |
| Microscopic appearance | AT | Identical to T0 | Identical to T0 | Identical to T0 | Identical to T0 |
|  | 40° C. | Identical to T0 | Identical to T0 | Identical to T0 | Identical to T0 |
| pH | AT | 5.98 | 5.96 | 5.87 | 5.84 |
|  | 40° C. | 5.56 | 5.37 | 4.81 | 4.55 |
| Haake rheology $4\ s^{-1}/20\ s^{-1}/100\ s^{-1}$ |  | N.R. | 223/310/379 | 245/328/385 | N.R. |
| Brookfield RVDVII+ (S29; 5 rpm) |  | N.R. | 196 042 cP | 189 880 cP | 187 610 cP |

Chemical Stability:

| | | Adapalene | | |
|---|---|---|---|---|
| | | | Time | |
| Stability conditions | | T0 | T1 M | T2 M |
| AT | g/g | 0.10 | 0.10 | 0.10 |
|  | % of the expected content | 100% | 100% | 100% |
| 40° C. | g/g | N.A. | 0.10 | 0.10 |
|  | % of the expected content |  | 100% | 100% |

Benzoyl Peroxide:

| | | | Time | |
|---|---|---|---|---|
| Stability conditions | | T0 | T1 M | T2 M |
| AT | g/g | 2.60 | 2.6 | 2.6 |
|  | % of the expected content | 104% | 104% | 104% |
| 40° C. | g/g | N.A. | 2.4 | 2.3 |
|  | % of the expected content |  | 96% | 92% |

Example 2

Formulation of Cream Type Comprising 0.3% Adapalene and 5% Benzoyl Peroxide

The formulation is prepared according to the procedure described above.

| Constituents | Content (% w/w) |
|---|---|
| Benzoyl peroxide | 5.00 |
| Adapalene | 0.30 |
| Dipropylene glycol | 5.00 |
| Synperonic PE/L44 | 0.20 |
| Glycerol | 7.00 |
| Xantural 180 | 0.40 |
| Eumulgin B2 PH | 3.00 |
| Arlacel 165FL | 3.00 |
| Speziol C18 Pharma | 2.00 |
| Mygliol 812 N | 7.00 |
| ST-Cyclomethine 5 NF | 6.00 |
| Simulgel 600 PHA | 2.50 |
| Purified water | q.s. for 100 |
| Sodium hydroxide | q.s. for pH 5.5 ± 0.5 |

Stability Data:
Physical Stability:

| Characterizations at T0 | | |
|---|---|---|
| Macroscopic appearance | | White cream |
| Microscopic appearance | | Dispersion of the active principles without aggregates >100 μm |
| pH | | 6.18 |
| Viscosity data | Haake ($4\ s^{-1}/20\ s^{-1}/100\ s^{-1}$) | 135/189/311 |
|  | Brookfield RVDVII+ (S29; 5 rpm) | 99 810 cP |

|  |  | T + 15 days | T + 1 month | T + 2 months | T + 3 months |
|---|---|---|---|---|---|
| Macroscopic appearance | AT | Identical to T0 | Identical to T0 | Identical to T0 | Identical to T0 |
|  | 40° C. | Identical to T0 | Identical to T0 | Identical to T0 | Identical to T0 |
| Microscopic appearance | AT | Identical to T0 | Identical to T0 | Identical to T0 | Identical to T0 |
|  | 40° C. | Identical to T0 | Identical to T0 | Identical to T0 | Identical to T0 |
| pH | AT | 5.78 | 5.39 | 5.35 | 5.14 |
|  | 40° C. | 4.36 | 4.12 | 3.82 | 3.74 |
| Haake rheology ($4\ s^{-1}/20\ s^{-1}/100\ s^{-1}$) |  | N.R. | N.R. | 117/190/287 | N.R. |
| Brookfield RVDVII+ (S29; 5 rpm) |  | N.R. | N.R. | 90 310 cP | 94 580 cP |

Chemical Stability:
Adapalene:

| | | | Time | |
|---|---|---|---|---|
| Stability conditions | | | T0 | T1 M |
| AT | g/g | | 0.29 | 0.29 |
|  | % of the expected content | | 96.66% | 96.66% |
| 40° C. | g/g | | N.A. | 0.29 |
|  | % of the expected content | |  | 96.66% |

Benzoyl Peroxide:

| | | | Time | |
|---|---|---|---|---|
| Stability conditions | | | T0 | T1 M |
| AT | g/g | | 5.10 | 5.10 |
|  | % of the expected content | | 102% | 102% |
| 40° C. | g/g | | N.A. | 4.70 |
|  | % of the expected content | |  | 94% |

Example 3

Formulation of Cream Type Comprising 0.1% Adapalene and 5% Benzoyl Peroxide

The formulation is prepared according to the procedure described above.

| Constituents | Content (% w/w) |
|---|---|
| Benzoyl peroxide | 5.00 |
| Adapalene | 0.10 |
| Propylene glycol | 6.00 |
| Synperonic PE/L44 | 0.20 |
| EDTA | 0.10 |
| Glycerol | 7.0 |
| Veegum K | 0.20 |

-continued

| Constituents | Content (% w/w) |
|---|---|
| Natrosol HHX | 0.20 |
| Eumulgin B2 PH | 3.0 |
| Speziol C18 Pharma | 2.0 |
| Miglyol 812 N | 7.0 |
| Arlacel 165FL | 3.0 |
| ST-Cyclomethicone 5 NF | 6.0 |
| Simulgel 600 | 2.0 |
| Purified water | q.s. for 100 |
| Triethanolamine | q.s. for pH 5.5 ± 0.5 |

Stability Data:

Physical Stability:

| Characterizations at T0 | |
|---|---|
| Macroscopic appearance | White cream |
| Microscopic appearance | Dispersion of the active principles without aggregates >100 μm |
| pH | 6.68 |
| Viscosity data | Haake (4 $s^{-1}$/20 $s^{-1}$/100 $s^{-1}$) 82/112/178 |

| | | T + 15 days | T + 1 month | T + 2 months | T + 3 months |
|---|---|---|---|---|---|
| Macroscopic appearance | AT | Identical to T0 | Identical to T0 | Identical to T0 | Identical to T0 |
| | 40° C. | Identical to T0 | Identical to T0 | Identical to T0 | Identical to T0 |
| Microscopic appearance | AT | Identical to T0 | Identical to T0 | Identical to T0 | Identical to T0 |
| | 40° C. | Identical to T0 | Identical to T0 | Identical to T0 | Identical to T0 |
| pH | AT | 5.80 | 5.85 | 5.59 | 5.47 |
| | 40° C. | N.R. | 4.41 | 4.13 | 3.82 |
| Haake rheology (4 $s^{-1}$/20 $s^{-1}$/100 $s^{-1}$) | | N.R. | N.R. | 69/108/168 | 61/95/168 |

Example 4

Formulation of Cream Type Comprising 0.3% Adapalene and 5% Benzoyl Peroxide

The formulation is prepared according to the procedure described above.

| Constituents | Content (% w/w) |
|---|---|
| Benzoyl peroxide | 5.00 |
| Adapalene | 0.30 |
| Dipropylene glycol | 5.00 |
| Synperonic PE/L44 | 0.20 |
| Glycerol | 7.00 |
| Xantural 180 | 0.40 |
| Eumulgin B2 PH | 3.00 |
| Arlacel 165FL | 3.00 |
| Speziol C18 Pharma | 2.00 |
| Mygliol 812 N | 7.00 |
| ST-Cyclomethicone 5-NF | 6.00 |
| Simulgel 600 PHA | 2.50 |
| Purified water | q.s. for 100 |
| Succinic acid + sodium succinate buffer | q.s. for pH 5.5 ± 0.5 |

Stability Data:

Physical Stability:

| Characterizations at T0 | |
|---|---|
| Macroscopic appearance | White cream |
| Microscopic appearance | Dispersion of the active principles without aggregates >100 μm |
| pH | 5.06 |
| Viscosity data | Haake (4 $s^{-1}$/20 $s^{-1}$/100 $s^{-1}$) 103/154/253 |

| | | T + 15 days | T + 1 month | T + 2 months | T + 3 months |
|---|---|---|---|---|---|
| Macroscopic appearance | AT | Identical to T0 | Identical to T0 | Identical to T0 | Identical to T0 |
| | 40° C. | Identical to T0 | Identical to T0 | Identical to T0 | Identical to T0 |
| Microscopic appearance | AT | Identical to T0 | Identical to T0 | Identical to T0 | Identical to T0 |
| | 40° C. | Identical to T0 | Identical to T0 | Identical to T0 | Identical to T0 |
| pH | AT | 4.86 | 4.82 | 4.66 | 4.59 |
| | 40° C. | N.R. | 3.80 | 3.62 | 3.45 |
| Haake rheology (4 $s^{-1}$/20 $s^{-1}$/100 $s^{-1}$) | | N.R. | N.R. | 72/123/215 | 97/156/245 |

Example 5

Formulation of Lotion Type Comprising 0.3% Adapalene and 1% Benzoyl Peroxide

The formulation is prepared according to the procedure described above.

| Constituents | Content (% w/w) |
|---|---|
| Benzoyl peroxide | 1.00 |
| Adapalene | 0.30 |
| Avicel CL-611 | 1.50 |
| Dipropylene glycol | 3.00 |
| Synperonic PE/L44 | 0.20 |
| Methylparaben | 0.15 |
| Brij 721 | 3.00 |
| Arlacel 165FL | 3.00 |
| Propylparaben | 0.05 |
| Perhydrosqualene | 5.00 |
| Cetiol SN PH | 5.00 |
| Simulgel 600 PHA | 1.50 |
| Purified water | q.s. for 100 |
| Triethanolamine | q.s. for pH 5.5 ± 0.5 |

Stability Data:

Physical Stability:

| Characterizations at T0 | |
|---|---|
| Macroscopic appearance | White lotion |
| Microscopic appearance | Dispersion of the active principles without aggregates >100 μm |
| pH | 5.534 |
| Viscosity data | Haake (4 $s^{-1}$/20 $s^{-1}$/100 $s^{-1}$) 23/40/88 |
| | Brookfield LVDVII+ (5 rpm; S63) 21 283 cP |

| | | T + 1 month | T + 2 months |
|---|---|---|---|
| Macroscopic appearance | AT | Identical to T0 | Identical to T0 |
| | 40° C. | Identical to T0 | Identical to T0 |
| Microscopic | AT | Identical to T0 | Identical to T0 |

-continued

| Characterizations at T0 | | | |
|---|---|---|---|
| appearance | 40° C. | Identical to T0 | Identical to T0 |
| pH | AT | 5.00 | 4.75 |
|  | 40° C. | 4.09 | 3.87 |
| Haake rheology 4 s⁻¹/20 s⁻¹/100 s⁻¹ |  | 18/35/69 | 17/27/63 |
| Brookfield LVDVII+ viscosity; (5 rpm; S63) |  | 15 861 cP | 14 637 cP |

Chemical Stability:
Adapalene:

| | Stability conditions | T0 | T + 1 month |
|---|---|---|---|
| AT | g/g | 0.29 | 0.29 |
|  | % of the expected content | 97 | 97 |
| 40° C. | g/g | N.A. | 0.28 |
|  | % of the expected content | N.A. | 93 |

Benzoyl Peroxide:

| | Stability conditions | T0 | T + 1 month |
|---|---|---|---|
| AT | g/g | 1.2 | 1.2 |
|  | % of the expected content | 120 | 120 |
| 40° C. | g/g | N.A. | 1.0 |
|  | % of the expected content | N.A. | 100 |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A stable dermatological emulsion comprising:
   2% to 50% by weight of at least one fatty phase;
   10% to 90% by weight of at least one hydrophilic phase comprising water;
   1% to 20% by weight of at least one emulsifier selected from the group consisting of (a) glyceryl stearate and PEG-100 stearate, (b) PEG-6 stearate and PEG-32 stearate, (c) polyoxyethylene (21) stearyl ether, (d) ceteareth-20, (e) PEG-20 methyl glucose sesquistearate, and (f) methyl glucose sesquistearate-type emulsifiers;
   0.01 to 5% by weight of dispersed adapalene as an active principle; and
   0.025% to 10% by weight of dispersed benzoyl peroxide as an active principle;
   wherein the emulsion is a homogeneous dispersion; and
   wherein the adapalene and the benzoyl peroxide are the only active principles in the emulsion.

2. The stable dermatological emulsion of claim 1, comprising from 0.01% to 1% by weight of adapalene.

3. The stable dermatological emulsion of claim 1, comprising from 1% to 10% by weight of benzoyl peroxide.

4. The stable dermatological emulsion as defined by claim 1, wherein the benzoyl peroxide is encapsulated.

5. The stable dermatological emulsion as defined by claim 1, wherein the benzoyl peroxide is in free form.

6. The stable dermatological emulsion of claim 1, wherein the emulsion further comprises from 0.01% to 15% by weight of one or more gelling agents and/or suspending agents and/or pH-independent gelling agents.

7. The stable dermatological emulsion of claim 1, wherein the emulsion further comprises up to 10% by weight of at least one wetting agent.

8. The stable dermatological emulsion of claim 1, wherein the emulsion further comprises up to 1.5% by weight of at least one chelating agent.

9. The stable dermatological emulsion of claim 1, comprising from 1% to 15% by weight of the at least one emulsifier.

10. The stable dermatological emulsion as defined by claim 1, wherein the emulsion is an oil-in-water emulsion.

11. The stable dermatological emulsion of claim 7, wherein the at least one wetting agent comprises dipropylene glycol, propylene glycol, Synperonic PE/L44 (a polyoxyethylene-polyoxypropylene block copolymer), or a combination thereof.

12. The stable dermatological emulsion of claim 1, comprising from 0.1% to 0.5% by weight adapalene.

13. The stable dermatological emulsion as defined by of claim 1, comprising 1% to 5% by weight benzoyl peroxide.

14. The stable dermatological emulsion of claim 1, comprising:
   from 0.1% to 0.5% by weight of adapalene;
   from 1% to 10% by weight of benzoyl peroxide;
   from 20% to 80% by weight of water;
   from 5% to 30% by weight of the at least one fatty phase; and
   from 3% to 11% by weight of the at least one emulsifier.

15. The stable dermatological emulsion of claim 1, comprising 0.1% to 1% by weight of adapalene and 1% to 10% by weight of benzoyl peroxide.

16. The stable dermatological emulsion of claim 1, comprising 0.1% or 0.3% by weight adapalene.

17. The stable dermatological emulsion of claim 1, comprising 1.0%, 2.5%, or 5.0% by weight benzoyl peroxide.

18. The stable dermatological emulsion of claim 6, wherein the at least one gelling agent and/or suspending agent and/or pH-independent gelling agent is selected from the group consisting of electrolyte-insensitive carbomers, xanthan gum, polyacrylamides, magnesium aluminum silicate, hydroxyethylcellulose, microcrystalline cellulose and carboxymethyl cellulose sodium, and combinations thereof.

19. The stable dermatological emulsion of claim 6, wherein the at least one gelling agent and/or suspending agent and/or pH-independent gelling agent is:
   (a) an electrolyte-insensitive carbomer; or
   (b) xanthan gum and sodium acryloyldimethyltaurate copolymer/isohexadecane/polysorbate 80 mixture; or
   (c) magnesium aluminum silicate, hydroxyethylcellulose, and sodium acryloyldimethyltaurate copolymer/isohexadecane/polysorbate 80 mixture; or
   (d) microcrystalline cellulose and carboxymethyl cellulose sodium mixture and sodium acryloyldimethyltaurate copolymer/isohexadecane/polysorbate 80 mixture.

20. The stable dermatological emulsion of claim 1, wherein the at least one fatty phase comprises:

(a) squalane and a silicone oil; or
(b) cetearyl isononanoate and squalane; or
(c) a fatty alcohol, caprylic/capric triglycerides, and a silicone oil.

21. The stable dermatological emulsion of claim 1, wherein the fatty phase comprises a silicone oil.

22. The stable dermatological emulsion of claim 21, wherein the fatty phase comprises a silicone oil selected from the group consisting of a dimethicone and a cyclomethicone.

23. The stable dermatological emulsion of claim 1, further comprising up to 20% by weight of at least one humectant and/or emollient.

24. The stable dermatological emulsion of claim 8, wherein the at least one chelating agent comprises EDTA.

25. The stable dermatological emulsion of claim 1, further comprising up to 3% by weight of at least one preservative.

26. The stable dermatological emulsion of claim 1, further comprising up to 3% by weight of at least one stabilizing agent.

27. The stable dermatological emulsion of claim 1, further comprising up to 10% by weight of at least one neutralizing agent.

28. The stable dermatological emulsion of claim 1, wherein the emulsion is formulated into a cream or a lotion.

29. The stable dermatological emulsion of claim 1, wherein the emulsion is physically, chemically, and rheologically stable over time at temperatures from 4° C. to 40° C. such that the macroscopic appearance and microscopic appearance of the emulsion after three (3) months is substantially identical to the macroscopic appearance and microscopic appearance of the emulsion at the time of formulation.

30. The stable dermatological emulsion of claim 1, wherein at least 90% of the benzoyl peroxide remains present in the composition after one month at temperatures from 4° C. to 40° C.

31. The stable dermatological emulsion of claim 1, wherein the at least one emulsifier is selected from the group consisting of (a) glyceryl stearate and PEG-100 stearate, (c) polyoxyethylene (21) stearyl ether, (d) ceteareth-20, (e) PEG-20 methyl glucose sesquistearate, and (f) methyl glucose sesquistearate-type emulsifiers.

32. The stable dermatological emulsion of claim 1, comprising from 50% to 85% by weight of water.

33. The stable dermatological emulsion of claim 6, comprising from 0.1% to 5% by weight of the at least one gelling agent and/or suspending agent and/or pH-independent gelling agent.

34. The stable dermatological emulsion of claim 23, wherein at least one humectant and/or emollient comprises glycerol.

* * * * *